United States Patent [19]

Washburn et al.

[11] Patent Number: 5,310,760

[45] Date of Patent: May 10, 1994

[54] 3,4-DISUBSTITUTED ANILINES-IMMUNOMODULATING AGENTS

[75] Inventors: William N. Washburn, Titusville, N.J.; Lee H. Latimer; Barbara B. Lussier, both of Rochester, N.Y.; Carl R. Illig, Phoenixville, Pa.; Alexander L. Weis, San Antonio, Tex.

[73] Assignee: Sterling Winthrop Inc., Malvern, Pa.

[21] Appl. No.: 89,007

[22] Filed: Jul. 9, 1993

Related U.S. Application Data

[63] Continuation of Ser. No. 816,504, Dec. 31, 1991, abandoned.

[51] Int. Cl.$^5$ .................. A61K 31/165; C07C 233/65
[52] U.S. Cl. .................. 514/619; 514/352; 514/517; 514/522; 514/534; 514/561; 546/304; 558/415; 560/45; 562/46; 562/433; 562/435; 564/163; 564/168
[58] Field of Search .............. 564/162, 163, 165, 168, 564/194, 167; 514/618, 619, 620, 622, 626, 617

[56] References Cited

U.S. PATENT DOCUMENTS

| | | | |
|---|---|---|---|
| 4,330,292 | 5/1982 | Bugaut et al. | 8/411 |
| 4,404,280 | 9/1983 | Gillis | 435/68 |
| 4,406,830 | 9/1983 | Fabricius | 435/240 |
| 4,738,927 | 4/1988 | Taniguchi et al. | 435/243 |
| 4,752,573 | 6/1988 | Ziegler et al. | 435/29 |
| 4,762,914 | 8/1988 | Auron et al. | 530/351 |
| 4,774,320 | 9/1988 | Tagliabue et al. | 530/328 |
| 4,780,313 | 10/1988 | Koichiro et al. | 424/88 |
| 4,789,658 | 12/1988 | Yoshimoto et al. | 514/12 |

FOREIGN PATENT DOCUMENTS 62-10049 1/1987 Japan.
63-239257 10/1988 Japan.

OTHER PUBLICATIONS

Gillis et al., Nature, 268, 154–156, 1977.
Farrar et al., J. Immunol., 121, 1353–1360, 1978.
Gillis et al., J. Immunol., 120, 2027–2033, 1978.
Gillis et al., J. Immunol., 124, 1954–1962, 1980.
Gillis et al., J. Immunol., 125, 2570–2578, 1980.
Gillis et al., J. Exp. Med., 152, 1709–1719, 1980.

Primary Examiner—Shailendra Kumar
Attorney, Agent, or Firm—Arthur Rosenstein; Imre Balogh

[57] ABSTRACT

Certain 3,4-disubstituted anilines and pharmaceutically acceptable salts thereof are provided which mimic IL-1 activity by inducing IL-2 synthesis and subsequent IL-2 receptor expression. Specifically, the invention provides compounds of Formula I and acid addition salts thereof:

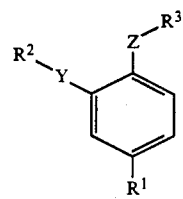

FORMULA I wherein
Y is

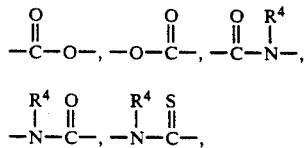

NHSO$_2$ or SO$_2$NH where R$^4$ is H;
Z is —O—, —NH—, —NR—, —S—, or other heteroatoms capable of hydrogen bonding with R$^4$ to give a preferred conformation;
R is alkyl;
R$^1$ is —NH$_2$ or —NHCH$_3$;
R$^2$ is H, alkyl, cycloalkyl, aralkyl, substituted or unsubstituted aryl, or a substituted or unsubstituted nitrogen heterocyclic group having 4 to 5 nuclear carbon atoms; and
R$^3$ is a lipophilic moiety.

8 Claims, No Drawings

3,4-DISUBSTITUTED ANILINES-IMMUNOMODULATING AGENTS

This application is a continuation of application Ser. No. 07/816,504, filed Dec. 31, 1991 now abandoned.

BACKGROUND OF THE INVENTION

1. Field of the Invention

The present invention relates to 3,4-disubstituted anilines, methods for their preparations and, to their use as immunomodulating agents. More specifically, the present invention relates to 3,4-disubstituted anilines having interleukin 1 (hereinafter IL-1) activity, which can be used as a stimulant of the immune functions.

2. Reported Developments

IL-1 is a 17kD polypeptide hormone which induces a wide range of biological effects by binding IL-1 to a specific receptor protein on responsive cells. Some of the activities of IL-1 include: induction of IL-2 secretion from T cells, induction of fibroblasts to secrete PGE, stimulation of osteoclasts to resorb bone, triggering the appearance of CSF receptors on stem cell progenitors, increasing synthesis of CSF's, activation of T and B cells, induction of cartilage destruction in joints, elevation of collagenase levels in synovial fluid and action as an endogenous pyrogen.

Because of the multiple activities of IL-1, a variety of uses for compounds influencing these responses have been envisioned. An IL-1 agonist or mimetic would have therapeutic applications as an immunostimulant, an anticancer agent or in inducing haemopoesis.

IL-1 has been produced in the prior art by inducing secretion thereof by normal macrophages/monocytes of peripheral blood by means of application of an inducing agent of bacterial origin. IL-1 has also been produced by culturing a human leukemic cell line of haematopoietic origin by means of application of phorbols as inducing agents. Another approach to provide for IL-1 activity is disclosed in U.S. Pat. No. 4,762,914 which teaches the production of truncated protein of IL-1 made by a genetic engineering procedure. The so obtained biologically active human IL-1 protein is said to be useful to induce the production of IL-2 by activated T-cells. Still another approach to provide IL-1 activity is disclosed in U.S. Pat. No. 4,774,320 which concerns the preparation and use of the following peptide that mimics human IL-1 activity:

Val-Gln-Gly-Glu-Glu-Ser-Asn-Asp-Lys-X where
X=cysteine (Cys), OH, $NH_2$, benzyl ester or an alkyl ester group having a number of carbon atoms from 1 to 7.

IL-2, also known as T cell growth factor, has been found to influence cell-mediated immune responses in mammals, such as: enhancement of thymocyte mitogenesis; production of cytotoxic T lymphocytes; promotion of proliferation of antigen specific killer T cell lines; and promotion of anti-erythrocyte placque forming cell responses.

Disruptions of the immunodefense system can be ascribed to the insufficient presence of IL-2 in the mammalian body, as a result of the lack of cells that produce IL-2, inadequate IL-2 production, or insufficient formation of IL-2 receptors (U.S. Pat. No. 4,752,573). In light of these findings by the prior art, IL-2 appears to be useful in promoting humoral and cellular immune responses and in restoring an immune deficient state to a normal immune state. Accordingly, IL-2 is indicated for medical immunotherapy against immunological disorders, including neoplastic diseases, bacterial or viral infections, immune deficient disorders and autoimmune diseases.

IL-2 has been produced in the prior art by stimulating mouse, rat or human lymphocytes with a mitogen (Gillis, S. et al., Nature, 268, 154–156, (1977), Farrat, J. et al., J. Immunol., 121, 1353–1360, (1978), Gillis, S. et al., J. Immunol., 120, 2027–2033, (1978)) or by stimulating human peripheral blood mononuclear lymphocytes with a mitogen (Gillis, S. et al., J. Immuno., 124, 1954–1962, (1980)). Gillis et al. reported the preparation of murine IL-2 from murine T cell lymphoma cell line (Gillis, S. et al. J. Immunol., 125, 2570–2578 (1980)) and preparation of human IL-2 from a human leukemia cell line (Gillis, S. et al., J. Exp. Med., 152, 1709–1719, (1980)).

Other methods of preparations, compositions and use thereof are illustrated by the following references.

U.S. Pat. No. 4,404,280 discloses a process for producing murine IL-2 from malignant neoplastic cells in vitro in a protein-containing medium. The process includes the utilization of IL-1 as a co-stimulant to induce IL-2 production.

U.S. Pat. No. 4,406,830 relates inter alia, to a process for producing a serum-free and mitogen-free IL-2 in vitro by adding glycoprotein to a serum-free and mitogen-free IL-1 preparation.

U.S. Pat. No. 4,738,927 discloses a method of producing IL-2 by isolating a gene which possesses IL-2 activity, connecting said gene with a vector DNA which is capable of replicating in a procaryotic or eucaryotic cell at a position down-stream of a promoter gene in the vector to obtain a recombinant DNA, with which the cell is transformed to produce IL-2.

U.S. Pat. No. 4,752,573 relates to the use of pterins to increase the activity of lymphokines and other cell growth factors, including IL-2.

U.S. Pat. No. 4,780,313 discloses a method for immunostimulating a warm-blooded animal by administering to said animal a substance having IL-2 activity, such as a recombinant non-glycosylated human IL-2, in combination with muramyldipeptide.

U.S. Pat. No. 4,789,658 relates to an immunoprophylactic and immunotherapeutic composition comprising grade E human IL-2 of human T-lymphocyte origin.

The utility of IL-2 to supplement immune responses and thus the need for IL-2 mediators to proliferate other effector cells, such as T-helper and suppressor cells, cytotoxic T-cells and natural killer cells (hereinafter NKC's) to promote cell-mediated immunity, is apparent from the above-described references.

It should also be noted that IL-1, or a biologically active compound that mimics IL-1 activity, plays a very important role as an immunostimulating agent by inducing IL-2 synthesis and subsequent IL-2 receptor expression.

We have now discovered a class of organic compounds which promote cell-mediated immunity based on their capability to elevate IL-2 and granulocyte macrophage colony stimulating factor (hereinafter GMCSF) levels in vitro and thus proliferate effector cells, such as cytotoxic T-cells lines and other subpopulations of T-cells.

SUMMARY OF THE INVENTION

In accordance with the present invention, certain 3,4-disubstituted anilines and pharmaceutically acceptable salts thereof are provided which mimic IL-1 activity by inducing IL-2 synthesis and subsequent IL-2 receptor expression. Specifically, the invention provides compounds of Formula I and acid addition salts thereof:

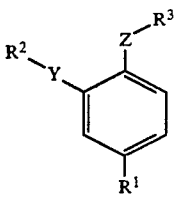

FORMULA I wherein
Y is

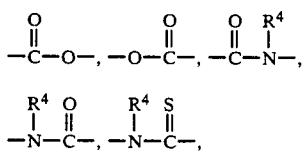

$NHSO_2$ or $SO_2NH$ where $R^4$ is H;
Z is —O—, —NH—, —NR—, —S—, or other heteroatoms capable of hydrogen bonding with $R^4$ to give a preferred conformation;
R is alkyl;
$R^1$ is —$NH_2$ or —$NHCH_3$;
$R^2$ is H, alkyl, cycloalkyl, aralkyl, substituted or unsubstituted aryl, or a substituted or unsubstituted nitrogen heterocyclic group having 4 to 5 nuclear carbon atoms; and
$R^3$ is a lipophilic moiety.

DETAILED DESCRIPTION OF THE INVENTION

As employed above and throughout the specification the following terms, unless otherwise indicated, shall be understood to have the following meaning:

The "alkyl" group per se and in alkoxy means a saturated or unsaturated aliphatic hydrocarbon which may be either straight- or branched-chained containing from one to about 10 carbon atoms. Lower alkyl is preferred having from one to six carbon atoms.

The "cycloalkyl" groups may be mono or polycyclic and contain 3 to 16 carbon atoms and include cyclopropyl, cyclobutyl, cyclopentyl, cyclohexyl, cycloheptyl and cyclooctyl. "Aryl" contains from 6 to 10 carbon atoms and include phenyl, tolyl, xylyl, naphthyl and the like.

"Substituted aryl" means an aryl group substituted by one or more lower alkyl, lower alkoxy, amino, lower alkyl amino, lower alkyl mercapto, hydroxy, hydroxy lower alkyl, acetoxy, benzyloxy, phenoxy, carboxy, carboalkoxy, halo, amido, halosulfonyl, lower alkyl sulfinyl or lower alkyl sulfonyl.

"Aralkyl" means an aromatic hydrocarbon radical containing from 7 to about 16 carbon atoms and include benzyl, phenethyl, naphthylmethyl and the like.

The "heterocyclic" groups may be mono or polycyclic and include such groups as pyridyl, pyrimidinyl, quinolyl, quinolinyl, piperidyl, pyrrolyl, morpholinyl, thiomorpholinyl, thiophenyl, furyl, furfuryl, thienyl, imidazolyl, benzimidazolyl, and the like. These groups may carry substitutents such as alkyl, alkenyl, alkynyl, hydroxy, thio, amino, alkylamino, dialkylamino, alkoxy, alkylthio and halo.

"Lipophilic" means a moiety having from about 1 to about 22 carbon atoms in the entire group and includes substituted or unsubstituted, straight-or branched-chain alkyl, cycloalkyl, neopentyl, nonyl, isononyl, alkyladamantyl, 2, 4-dimethylbenzyl, substituted or unsubstituted phenyl, such as 2, 4-di-t-pentylphenyl or 2-naphthyl with the proviso that when $R^3$ is substituted phenyl, there can be up to three lipophilic substitutents such as a halo, alkyl, cycloalkyl, alkoxy, carbalkoxy such as carbomethoxy, carbobutoxy, isobutoxy or amido such as acetamido or propionamido.

When $R^2$ is substituted aryl it can have up to five of the lipophilic substituents described under "lipophilic" above or any combination of members of said lipophilic group with a polar substitutent, such as cyano, amino, hydrazino, acetylhydrazino, arylazo, fluorosulfonyl or carboxamido.

"Halogen" means Cl, F, I or Br.

Preferred compounds of this invention are aryloxyanilides having the structure of Formula II:

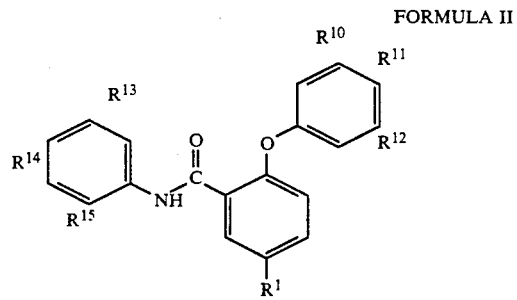

FORMULA II wherein
$R^1$ is —$NH_2$ or —$NHCH_3$;
$R^{10}$, $R^{11}$ and $R^{12}$ are independently H or a lipophilic group, or any two of $R^{10}$, $R^{11}$ and $R^{12}$ can be taken together with the phenyl nucleus to which they are attached to form a $\beta$-naphthyl group; and
$R^{13}$, $R^{14}$ and $R^{15}$ are independently H, a lipophilic group or a polar group.

Still more preferred compounds are: N-(isopropyl)-5-amino-2-(2,4-bis(1,1-dimethylpropyl)phenoxy)benzamide, phenyl-5-amino-2-(2,4-bis(1,1-dimethylpropyl)-phenoxy)-benzanilide, 5-amino-2-(2,4-bis(1,1-dimethylpropyl)phenoxy)-benzanilide hydrochloride, 5-amino-2-(2,4-bis(1,1-dimethylpropyl)phenoxy)-benzanilide methansulfonic acid salt, 3'-carbomethoxy-5-amino-2-(2,4-bis(1,1-dimethylpropyl)phenoxy)-benzanilide, 4'-methyl-5-amino-2-(2,4-bis(1,1-dimethylpropyl)phenoxy)-benzanilide, 4'-fluoro-5-amino-2-(2,4-bis(1,1-dimethylpropyl)phenoxy)-benzanilide, 4'-iodo-5-amino-2-(2,4-bis(1,1-dimethylpropyl)phenoxy)-benzanilide, 4'-carbomethoxy-5-amino-2-(2,4-bis(1,1-dimethylpropyl)-phenoxy)-benzanilide, 2',6'-dimethyl-5-amino-2-(2,4-bis(1,1-dimethylpropyl)phenoxy)-benzanilide, 3',5'-dichloro-5-amino-2-(2,4-bis(1,1-dimethylpropyl)-phenoxy)-benzanilide, 3',5'-dicarbomethoxy-5-amino-2-(2,4-bis(1,1-dimethylpropyl)phenoxy)-benzanilide, 5-amino-2-(2-(1,1-dimethylethyl)-4-methoxyphenoxy)-benzanilide, 4'-(1,1-dimethylethyl)-5-amino-2-(2,4- bis(1,1-dimethylpropyl)phenoxy)-benzanilide, 4'-cyano-5-amino-2-(2,4-bis(1,1-dimethylpropyl)phenoxy)-benzanilide, 4'-(carbo-n-butoxy)-5-amino-2-(2,4-bis(1,1-dimethylpropyl)phenoxy)-benzanilide, 4'-amino-5-amino-2-(2,4-bis(1,1-dimethylpropyl)phenoxy)-benzanilide, 2',5'-dicarbomethoxy-5-amino-2-(2,4-bis(1,1-dimethylpropyl)phenoxy)-benzanilide, 3',5'-bis(trifluoromethyl)-5-amino-2-(2,4-bis(1,1-dimethylpropyl)phenoxy)-benzanilide, 3',5'-dicarbo-(1,1-dimethylethoxy)-5-amino-2-(2,4-bis(1,1-dimethylpropyl)phenoxy)-benzanilide and 4'-(3-(3-ethylglutarimide))-5-amino-2-(2,4-bis(1,1-dimethylpropyl)phenoxy)-benzanilide.

The compounds of the present invention may be prepared by the following schemes:

SCHEME 1

[Structure 1: 2-chloro-5-nitrobenzoic acid] →NaOAr→

[Structure 2] 1) SOCl₂ or (COCl)₂ / 2) RNH₂ →

[Structure 3]

H₂/Cat/THF →

[Structure 4-56]

wherein R is alkyl or substituted aryl. Substituents on the aryl include alkyl, aryl, fused aryl, alkoxy, carbo alkoxy, cyano, amido, halo, amino, and nitro in the ortho, meta and para positions.

The process depicted in Scheme 1 is a follows:

2-Chloro-5-nitrobenzoic acid 1 was coupled with the sodium salt of the desired phenol to yield the benzoic acid intermediate 2. The acid chloride was prepared via treatment of the carboxylic acid 2 with oxalyl chloride or thionyl chloride and was subsequently reacted with the desired amine. The resulting amide 3 was catalytically reduced with hydrogen and palladium on carbon catalyst providing the target molecules identified in Tables 1, 2 and 3.

TABLE 1

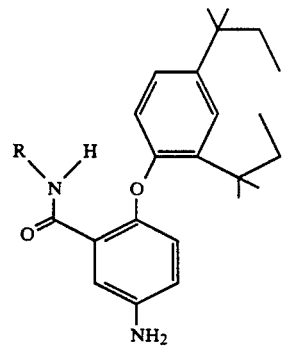

| COMPOUND NO. | R |
|---|---|
| 4 | H |
| 5 | CH₂CH₃ |
| 6 | CH₂CH₂NH₂ |
| 7 | CH(CH₃)₂ |
| 8 | (CH₂CH₃)₂ |
| 9 | CH₂Phenyl |
| 10 | CH₂CH₂Phenyl |
| 11 | Cyclohexyl |
| 12 | 3-Pyridyl |
| 13 | Phenyl |

TABLE 2

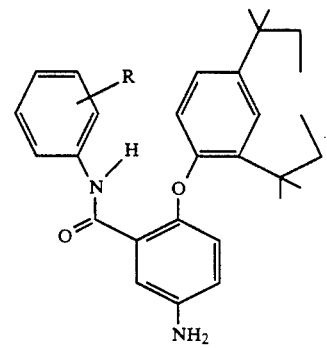

| COMPOUND NO. | R |
|---|---|
| 14 (a) | H |
| 15 (b) | H |
| 16 | 2-CH₃ |
| 17 | 2-COOCH₃ |
| 18 | 3-CH₃ |
| 19 (c) | 3-COOH |
| 20 | 3-COOCH₃ |
| 21 | 4-CH₃ |
| 22 | 4-CF₃ |
| 23 | 4-C(CH₃)₃ |
| 24 | 4-OCH₃ |
| 25 | 4-F |
| 26 | 4-I |
| 27 (d) | 4-OH |
| 28 | 4-CN |
| 29 | 4-CH₂OCH₃ |
| 30 | 4-Phenyl |
| 31 (e) | 4-COOH |
| 32 | 4-COOCH₃ |
| 33 | 4-COO(CH₂)₃CH₃ |
| 34 | 4-NH₂ |
| 35 | 4-N(CH₃)₂ |
| 36 | 4-NHCOCH₃ |
| 37 (a) | 4-NHCOCH₃ |
| 38 | 4-SO₃H |
| 39 | 4-SO₂F |
| 40 | 4-SO₂NH₂ |
| 41 | 2,5-(COOCH₃)₂ |

TABLE 2-continued

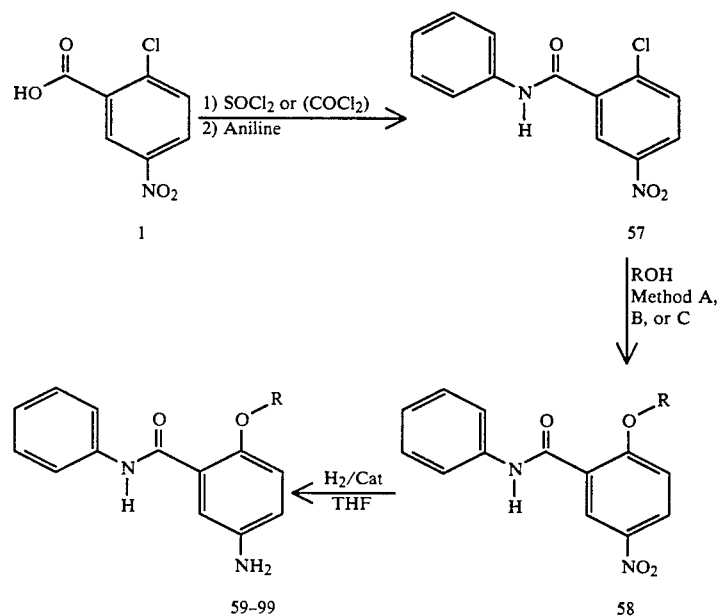

| COMPOUND NO. | R |
|---|---|
| 42 | 2,6-(CH$_3$)$_2$ |
| 43 | 3,4-(COOCH$_3$)$_2$ |
| 44 | 3,5-(CH$_3$)$_2$ |
| 45 | 3,5-(CF$_3$)$_2$ |
| 46 | 3,5-(OCH$_3$)$_2$ |
| 47 | 3,5-Cl$_2$ |
| 48 | 3,5-(COOCH$_3$)$_2$ |
| 49 | 3,5-(COOCH(CH$_3$)$_2$)$_2$ |
| 50 | 4-3-(3-Ethyl-glutarimide) | a) Isolated as HCl salt.
b) Isolated as CH$_3$SO$_3$H salt.
c) Prepared by base hydrolysis of the methyl ester.
d) Prepared by BBr$_3$ deprotection of the methyl ether.
e) Prepared by base hydrolysis of the methyl ester.

TABLE 3

| COMPOUND NO. | R |
|---|---|
| 51 | H |
| 52 | 2,5-(C(CH$_3$)$_3$)$_2$ |
| 53 | 3,5-(OCH$_3$)$_2$ |
| 54 | 3,5-(COOCH$_3$)$_2$ |
| 55 | 3,4,5-(OCH$_3$)$_3$ |
| 56 | 4-(CH$_2$)$_5$CH$_3$ |

SCHEME 2

Method A: TMG/DMA
Method B: NaH/DMF
Method C: K$_2$CO$_3$/Acetone

Scheme 2 illustrates the synthetic route to the compounds listed in Table 4. The acid chloride of the benzoic acid 1 was prepared with oxalyl chloride or thionyl chloride and subsequently reacted with aniline to ·rovide the intermediate 2-chloro-5-nitrobenzamide 57 in good yield. Three methods were employed to couple 57 with the desired alcohol or phenol depending on ease of reaction and/or the presence of sterically hindering groups to provide the 2-substituted-5-nitrobenzamides 58. Method A: tetramethylguanadine (TMG) and N,N-dimethylacetamide (DMA), was generally used for phenols. Method B: NaH in DMF was used for hindered phenols and alkyl alcohols. The p-hydroxybenzoic acid derivative 82 was prepared by Method C. The 2-substituted-5-nitrobenzamides 58 were catalytically reduced to the target anilines listed in Table 4 in generally good to quantitative yield.

TABLE 4

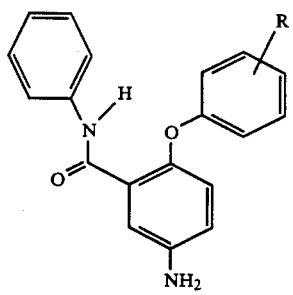

| COMPOUND NO. | R |
|---|---|
| 59 | 2-$CH_3$ |
| 60 | 2-$OCH_3$ |
| 61 | 2-$C(CH_3)_3$ |
| 62 | 2-$NHCOCH_3$ |
| 63 | 3-$CH_3$ |
| 64 | 3-$CF_3$ |
| 65 | 3-$C(CH_3)_3$ |
| 66 | 2-CN |
| 67 | 3-O-Phenyl |
| 68 | 3-$NH_2$ |
| 69 | 3-$N(CH_2CH_3)_2$ |
| 70 | 3-$NHCOCH_3$ |
| 71 | 4-$CH_3$ |
| 72 | 4-$OCH_3$ |
| 73 | 4-$C(CH_3)_2CH_2CH_3$ |
| 74 | 4-$C(CH_3)_2CH_2C(CH_3)_3$ |
| 75 | 4-$CF_3$ |
| 76 | 4-Cl |
| 77 | 4-F |
| 78 | 4-$NH_2$ |
| 79 | 4-$N(CH_3)_2$ |
| 80 | 4-$NHCOCH_3$ |
| 81 (a) | 4-$NHCOCH_3$ |
| 82 | 4-COOH |
| 83 | 4-$COOCH_3$ |
| 84 | 4-$CONH_2$ |
| 85 | 4-Phenyl |
| 86 (a) | 4-Phenyl |
| 87 | 2,4-$(CH_3)_2$ |
| 88 | 2,4-$((CH_2)_4CH_3)_2$ |
| 89 | 2,4-$(C(CH_3)_3)_2$ |
| 90 | 2,4-$(C(CH_3)_2CH_2C(CH_3)_3)_2$ |
| 91 | 2-$C(CH_3)_3$-4-$OCH_3$ |
| 92 | 2-$CH(CH_3)_2$-4-$C(CH_3)_2(OH)$ |
| 93 | 2,5-$(C(CH_3)_3)_2$ |
| 94 | 2,5-$(CH_3)_2$ |
| 95 | 2,6-$(CH(CH_3)_2)_2$ |
| 96 | 3,5-$(CH_3)_2$ |
| 97 | 2,4,6-$(CH_3)_3$ |
| 98 | 1-Naphthyl |
| 99 | 2-Naphthyl |

(a) Isolated as the HCl salt.

SCHEME 3

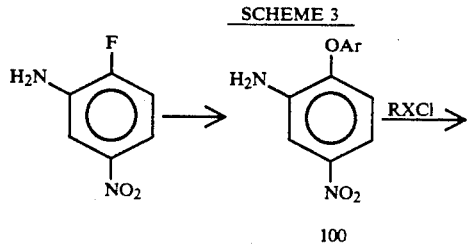

-continued
SCHEME 3

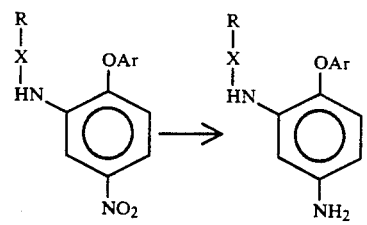

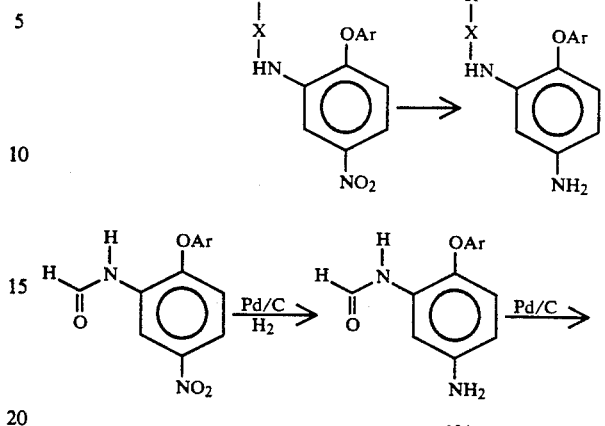

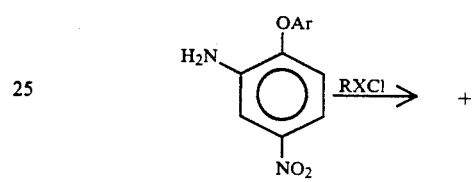

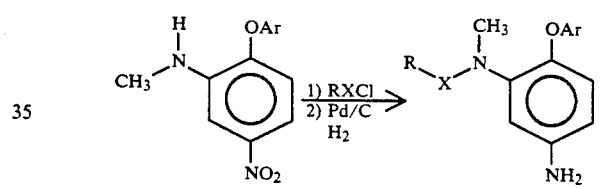

Ar = 2,4-di-pentyl
X = Co or $SO_2$

Scheme 3 illustrates the synthetic route to the compounds listed in Table 5.

Aryl ether 100 was prepared from 2-fluoro-5-nitroaniline and the desired phenol. Reaction with the desired acid chloride or sulfonyl chloride provided generally good yields of compounds like 101 which upon catalytic reduction with hydrogen and palladium on carbon as catalyst provided the target compounds like 102 in fair to quantitative yield. Alternatively, the aryl ether 100 was treated with triethyl orthoformate and the resulting alkoxy imine reduced with borane-tetrahydrofuran complex to yield the N-methyl compound 103 plus a significant amount of formamide 108. Catalytic reduction of the nitro group with hydrogen and palladium on carbon as catalyst (10%Pd/C in THF) led to 105. The N-methyl amine 103 was first treated with the desired acid chloride or sulfonyl chloride and then catalytically reduced to compounds 106–114. The sulfonamide 114 was prepared from 2-chloro-5-nitrobenzenesulfonic acid and the desired phenol.

Compound 100 can also be produced by the following route:

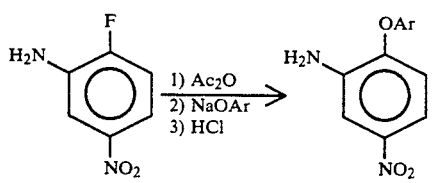

followed by the above-stated procedure to obtain compounds 106–114.

TABLE 5

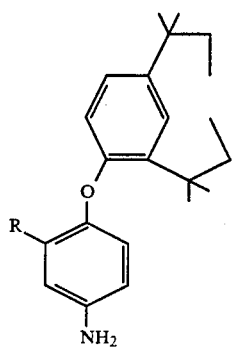

| COMPOUND NO. | R |
|---|---|
| 106 | NHCOCH$_2$CH$_3$ |
| 107 | NHCO-Phenyl |
| 108 | NHCO(2-CH$_3$-Phenyl) |
| 109 | NHCO(3,4,5-(OCH$_3$)$_3$-Phenyl) |
| 110 | NHCO(3,5-(OCH$_3$)$_2$-Phenyl) |
| 111 | N(CH$_3$)CO-Phenyl |
| 112 | NHSO$_2$-Phenyl |
| 113 | N(CH$_3$)SO$_2$-Phenyl |
| 114 | SO$_2$NH-Phenyl |

Table 6 shows compounds prepared using appropriate starting materials and a method analogous to that of Scheme 3.

TABLE 6

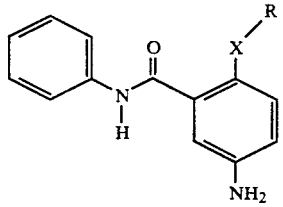

| COMPOUND NO. | X | R |
|---|---|---|
| 115 (a) | OCH$_3$ | 2,4-(CH$_3$)$_2$-phenyl |
| 116 | 2-CH$_3$-piperidyl | |
| 117 | 4-CH$_3$-piperidyl | |

(a) Isolated as the HCl salt

The following preparative examples will further illustrate the invention.

EXAMPLE 1

4'-Methyl-5-amino-2-(2,4-bis(1,1-dimethylpropyl)-phenoxy)-benzanilide

A) To 18.0 g (45.1 mmol) of 2-(2,4-di-(1,1-dimethylpropyl)phenoxy)-5-nitrobenzoic acid suspended in 75 ml of CH$_2$Cl$_2$ was added 5.64 ml (63.1 mmol, 1.4 eq) of oxalyl chloride followed by 2 drops of DMF and the reaction stirred for 2 hrs. at room temperature. The reaction mixture was then concentrated under vacuum to an orange oil. The oil was diluted with CH$_2$Cl$_2$ to a volume of 80 ml and partitioned into 8 fractions of 9.6 ml for later use.

One portion of the acid chloride solution was added to a solution of 0.638 g (5.95 mmol, 1.1 eq) of 4-methylaniline in 15 ml of CH$_2$Cl$_2$ at room temperature. To this solution was added 1.13 ml (8.12 mmol, 1.5 eq) of triethylamine. The solution turned yellow and a precipitate appeared over 5 min. After 10 min. the solution was concentrated under vacuum and dissolved in 80 ml of ether. The organic solution was washed twice with 1M HCl, then with saturated NaHCO$_3$, brine and the organic layer dried over Na$_2$SO$_4$. Removal of the solvent under vacuum yielded 2.80 g of yellow foam. The nitro amide intermediate was obtained as a yellow powder from cold etherhexane, 2.25 g (85%).

B) The nitro amide is hydrogenerated to the aniline as follows: To 1.25 g (2.56 mmol) of the nitro amide in 50 ml of ethyl acetate was added 0.13 g of 5% Pd on carbon and the mixture placed on a Parr hydrogenation apparatus at 45 psi. An additional 0.05 g of catalyst was added after 2 hrs. and the reaction continued for 14 hrs. The catalyst was filtered off and the filtrate concentrated under vacuum to yield a white solid. Recrystallization from ether-hexane gave 1.08 g (87%) of the title product.

Employing the procedure of Example 1 the following compounds can be made:

4'-carbomethoxy-5-amino-2-(2,4-bis(1,1-dimethylpropyl)phenoxy)-benzanilide;

4'-iodo-5-amino-2-(2,4-bis(1,1-dimethylpropyl)phenoxy)-benzanilide;

2',6'-dimethyl-5-amino-2-(2,4-bis(1,1-dimethylpropyl)-phenoxy)-benzanilide; and

3',5'-dicarbomethoxy-5-amino-2-(2,4-bis(1,1-dimethylpropyl)phenoxy)-benzanilide.

EXAMPLES 2–7

To 3.0 g (10.8 mmol) of 2-chloro-5-nitrobenzanilide in 20 ml of dimethylacetamide (DMA) is added 1.8 g (12 mmol) of a phenol compound of Formula A, Formula A wherein:

| R | Example |
|---|---|
| 2-C(CH$_3$)$_2$CH$_2$CH$_3$ | 2 |
| 4-C(CH$_3$)$_2$CH$_2$CH$_3$ | 3 |
| 2,4-(C(CH$_3$))$_2$CH$_2$CH$_3$)$_2$ | 4 |
| 2,4-(C(CH$_3$)$_2$CH$_2$(CH$_3$)$_3$)$_2$ | 5 |
| 2-C(CH$_3$)$_3$-4-OCH$_3$ | 6 |
| 2,5-(C(CH$_3$)$_3$)$_2$ | 7 |

After complete dissolution, 2.0 ml of tetramethylguanidine (TMG) is added all at once. The reaction mixture is stirred for 16 hrs. Workup consists of dilution with 100–150 mls of ethyl acetate and washing with water (to remove TMG hydrochloride, the solid which sometimes appears in the reaction flask). Washing quickly with 1N NaOH removes residual phenol and a final washing with saturated NaHCO$_3$ (to buffer the pH down) removes any hydrolysed ethyl acetate. A final wash with saturated NaCl might be used as well. Drying is done over $Na_2SO_4$ and the solvent removed at reduced pressure to yield either an oil or solid. Recrystallization from acetone/ligroin yields the intermediate nitro amide of Formula B in the form of white crystals wherein R denotes the same radicals as in Formula A:

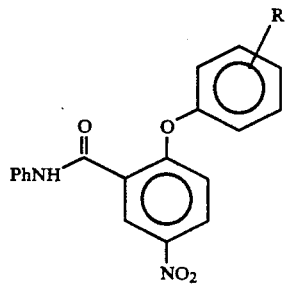

Formula B

Yields are 80-95% from 2-3 crystallization fractions.

The nitro amides are then hydrogenated as described in Example 1B to yield about 85% of the following anilines:

| Example | Anilines |
|---|---|
| 2 | 5-amino-2-(2(1,1-dimethylpropyl)phenoxy)-benzanilide |
| 3 | 5-amino-2-(4-(1,1-dimethylpropylphenoxy)-benzanilide |
| 4 | 5-amino-2-(2,4-bis(1,1-dimethylethylphenoxy)-benzanilide |
| 5 | 5-amino-2-(2,4-bis(1,1,3,3-tetramethylbutyl)phenoxy)-benzanilide |
| 6 | 5-amino-2-(2-(1,1-dimethylethyl)-4-methoxyphenoxy)-benzanilide |
| 7 | 5-amino-2-(2,5-bis(1,1-dimethylethyl)phenoxy)-benzanilide |

EXAMPLE 8

5-Amino-2-(2,4-dimethylbenzyloxy)-benzanilide

To 0.420 g (1.3 eq) of an 80% dispersion of sodium hydride in 20 ml of dry dimethylformamide (DMF) is added 2.0 g of 2,4-dimethylbenzyl alcohol in a small amount of DMF with care to avoid too rapid gas ($H_2$) evolution. The solution is stirred 15 min. beyond the end of gas evolution and 3.0 g (10.8 mmol, 1.0 eq.) of 2-chloro-5-nitrobenzanilide is added as a solid. After completion, the reaction mixture is poured into water and extracted twice with ethyl acetate. The organics are combined, washed quickly with 1N NaOH, water, and dried with $Na_2SO_4$. After removal of the solvent, the nitro amide intermediate is recrystallized from acetone/ligroin. Yield is 3.519 g (86%).

The nitro amide (1.0 g) is then hydrogenated as described in Example 1B to yield 0.606 g (66%) of the title compound.

The biological profile of the compounds of the present invention include the following characteristics:

(a) Induction of secretion of IL-2 by murine EL-4 cells at concentrations as low as $4 \times 10^{-8}M$;

(b) Induction of IL-2 and granulocytes macrophage colony stimulating factor (GM-CSF) gene expression in EL-4 cells;

(c) Production of IL-3 and IL-4;

(d) Lack of binding IL-1, IL-2 or IL-4 receptors; neither agonists or antagonists to these lymphokines;

(e) Induction of proliferation of human thymocytes;

(f) Induction of proliferation of human T-cells and B-cells and murine T-cells;

(g) No indication of toxicity when administered IP, PO or IV; and (h) Enhancement of human mixed lymphocyte reaction in a dose-dependent manner.

Based on these findings, the compounds of the present invention are useful for prophylaxis and therapy of immunological diseases. According to the kind of diseases, to the condition of the patients and to the immune state, the physician will determine the amount of the drug to be administered, the frequency of administration, routes of administration and vehicles containing the compounds to be administered.

The compounds of this invention can be normally administered parenterally, in the prophylaxis and treatment of immunological disorders.

The compounds of this invention, preferably in the form of a salt, may be formulated for administration in any convenient way, and the invention includes within its scope pharmaceutical compositions containing at least one compound according to the invention adapted for use in human or veterinary medicine. Such compositions may be formulated in a conventional manner using one or more pharmaceutically acceptable carriers or excipients. Suitable carriers include diluents or fillers, sterile aqueous media and various non-toxic organic solvents.

For parenteral administration, solutions or suspensions of these compounds in aqueous alcoholic media or in sesame or peanut oil or aqueous solutions of the soluble pharmaceutically acceptable salts described herein can be employed. Solutions of the salts of these compounds are especially suited for intramuscular and subcutaneous injection purposes. The aqueous compositions, including solutions of the salts dissolved in pure distilled water are also useful for intravenous injection purposes, provided that their pH is properly adjusted, suitably buffered, made isotonic with sufficient saline or glucose and sterilized by heating or by microfiltration. Certain compositions useful for intravenous injection or infusion may be prepared using the solid form of the active compound of the present invention. The solid compound may be suspended in propylene glycol, or a polyethylene glycol ether such as PEG 200, using a sonicator and the resulting mixture combined with aqueous media.

The dosage regimen in carrying out the methods of this invention is that which insures maximum therapeutic response until improvement is obtained and thereafter the minimum effective level which gives relief. It should be borne in mind that selecting the appropriate dosage in any specific case, consideration must be given to the patient's weight, general health, age and other factors which may influence response to the drug. The drug may be administered as frequently as is necessary to achieve and sustain the desired therapeutic response.

The present invention is also useful as an injectable dosage form which may be administered in an emergency to a patient. Such treatment may be followed by intravenous infusion of the active compound and the amount of compound infused into such patient should be effective to achieve and maintain the desired therapeutic response.

The following test results illustrate the beneficial effects of compounds of the present invention.

IL-1 BIOASSAY

EL-4 6.1 cells (murine T-cells) were first treated with mitomycin C to inhibit their proliferation. After washing the cells free of mitomycin C, the test compound ($10^{-5}$M) or the IL-1 standard ($3\times10^{-11}$M) was incubated with $2\times10^5$ EL-4 6.1 cells for 24 hours to allow gene expression and IL-2 synthesis. To quantify IL-2 production, CTLL-2 cells (IL-2 hybridized mouse cytotoxic T cell line which requires IL-2 for growth) were added and incubated for 24 hours; then tritiated thymidine was added and the cells incubated an additional 4 hours. The cells were then collected by centrifugation through oil and counted. Screening results were reported relative to the IL-1 standard run concurrently. Activity was considered to be >20% cell proliferation of the IL-1 standard as determined by thymidine uptake. Positive compounds that demonstrated reproducible biological activity were then tested for a dose response at $10^{-5}$, $3\times10^{-6}$, $10^{-6}$ and $4\times10^{-7}$M and $4\times10^{-8}$M. The result in Table 7 gives the activity indicated where the numbers refer to compound numbers and the activity key is as shown:

| | |
|---|---|
| + | Active at $10^{-5}$ M |
| ++ | Active at $3\times10^{-6}$ M |
| +++ | Active at $10^{-6}$ M |
| ++++ | Active at $4\times10^{-7}$ M |
| +++++ | Active at $10^{-7}$ M |
| ++++++ | Active at $4\times10^{-8}$ M |

TABLE 7

| COMPOUND NO. | ACTIVITY |
|---|---|
| 4 | + |
| 5 | +++ |
| 7 | ++++ |
| 8 | + |
| 9 | +++ |
| 10 | ++ |
| 11 | +++ |
| 12 | ++ |
| 13 | ++++ |
| 14 | ++++ |
| 15 | ++++ |
| 16 | +++ |
| 17 | ++ |
| 18 | +++ |
| 20 | ++++ |
| 21 | ++++ |
| 22 | ++ |
| 23 | ++ |
| 24 | +++ |
| 25 | ++++ |
| 26 | +++++ |
| 27 | +++ |
| 28 | ++ |
| 29 | +++ |
| 30 | +++ |
| 32 | ++++ |
| 33 | ++ |
| 34 | ++ |
| 35 | +++ |
| 37 | + |
| 39 | +++ |
| 41 | ++ |
| 42 | ++++ |
| 43 | +++ |
| 44 | +++ |
| 45 | ++ |
| 46 | +++ |
| 47 | ++++ |
| 48 | ++++ |
| 49 | ++ |
| 50 | ++ |
| 51 | + |
| 52 | + |
| 53 | + |
| 59 | ++ |
| 61 | +++ |
| 63 | + |

TABLE 7-continued

| COMPOUND NO. | ACTIVITY |
|---|---|
| 64 | ++ |
| 65 | ++ |
| 71 | + |
| 72 | + |
| 73 | +++ |
| 74 | ++ |
| 75 | + |
| 76 | + |
| 77 | ++ |
| 83 | + |
| 85 | +++ |
| 86 | +++ |
| 88 | + |
| 89 | +++ |
| 90 | +++ |
| 91 | ++++ |
| 92 | + |
| 93 | +++ |
| 94 | ++ |
| 95 | ++ |
| 96 | ++ |
| 97 | ++ |
| 99 | ++ |
| 106 | + |
| 108 | ++ |
| 109 | + |
| 112 | + |
| 113 | + |
| 114 | +++ |
| 115 | ++ |

It should be understood by those skilled in the art that various modifications may be made in the present invention without departing from the spirit and scope thereof as described in the specification and defined in the appended claims.

What is claimed is:

1. An immunomodulating compound or a pharmaceutically acceptable salt thereof having the formula

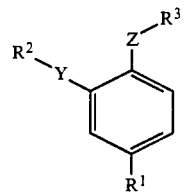

wherein
Y is

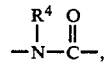

where $R^4$ is H;
Z is —O—
$R^1$ is —NH$_2$ or —NHCH$_3$;
$R^2$ is substituted or unsubstituted phenyl wherein said substituents are selected from the group consisting of lower alkyl, lower alkoxy, amino, lower alkyl amino, hydroxy, hydroxy lower alkyl, and halo; and
$R^3$ is substituted phenyl,
wherein said substituted phenyl contains no more than three substituents selected from the group consisting of halo, $C_3$-$C_{10}$alkyl, cycloalkyl and alkoxy.

2. The immunomodulating compound of claim 1 wherein said substituent for phenyl is —Cl, —F, —I or —Br.

3. The immunomodulating compound of claim 1 wherein $R^2$ is substituted phenyl having up to five substituents thereon selected from the group consisting of halo, lower alkyl and lower alkoxy.

4. The immunomodulating compound of claim 1 selected from the group consisting of 4'-methyl-5-amino-2-(2,4-bis(1,1-dimethylpropyl)phenoxy)-benzanilide, 5-amino-2-(2,4-bis(1,1-dimethylpropyl)phenoxy)-benzanilide hydrochloride, 4'-methyl-5-amino-2-(2,4-bis(1,1-dimethylpropyl)phenoxy)-benzanilide, 4'-fluoro-5-amino-2-(2,4-bis(1,1-dimethylpropyl)phenoxy)-benzanilide, 4'-fluoro-5-amino-2-(2,4-bis(1,1-dimethylpropyl)phenoxy)-benzanilide, 4'-iodo-5-amino-2-(2,4-bis(1,1-dimethylpropyl)phenoxy)-benzanilide, and 2',6'-dimethyl-5-amino-2-(2,4-bis(1,1-dimethylpropyl)phenoxy)-benzanilide.

5. The immunomodulating compound of claim 1 selected from the group consisting of 3',5'-dichloro-5-amino-2-(2,4-bis(1,1-dimethylpropyl)phenoxy)-benzanilide, 5-amino-2-(2-(1,1-dimethylethyl)-4-methoxyphenoxy)-benzanilide, 4'-(1,1-dimethylethyl)-5-amino-2-(2,4-bis(1,1-dimethylpropyl)-phenoxy)-benzanilide and 4'-amino-5-amino-2-(2,4-bis(1,1-dimethylpropyl)phenoxy)-benzanilide.

6. A pharmaceutical composition comprising a therapeutically effective amount of an immunomodulating compound having the formula

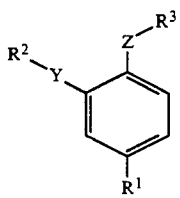

wherein

Y is

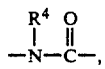

where $R^4$ is H;

Z is —O—

$R^1$ is —NH$_2$ or —NHCH$_3$;

$R^2$ is substituted or unsubstituted phenyl wherein said substituents are selected from the group consisting of lower alkyl, lower alkoxy, amino, lower alkyl amino, hydroxy, hydroxy lower alkyl, and halo; and $R^3$ is substituted phenyl wherein said substituted phenyl contains no more than three substituents selected from the group consisting of halo, $C_3$–$C_{10}$ alkyl, cycloalkyl and alkoxy, in combination with pharmaceutically acceptable carrier.

7. The pharmaceutical composition of claim 6 wherein said immunomodulating compound is selected from the group consisting of phenyl-5-amino-2-(2,4-bis(1,1-dimethylpropyl)phenoxy)-benzanilide, 5-amino-2-(2,4-bis(1,1-dimethyl-propyl)phenoxy)-benzanilide hydrochloride, 4'-methyl-5-amino-2-(2,4-bis(1,1-dimethylpropyl)phenoxy)-benzanilide, 4'-fluoro-5-amino-2-(2,4-bis(1,1-dimethylpropyl)phenoxy)-benzanilide, 4'-iodo-5-amino-2-(2,4-bis(1,1-dimethylpropyl)phenoxy)-benzanilide and 2',6'-dimethyl-5-amino-2-(2,4-bis(1,1-dimethylpropyl)phenoxy)-benzanilide.

8. The pharmaceutical composition of claim 6 wherein said immunomodulating compound is selected from the group consisting of 3', 5'-dichloro-5-amino-2-(2,4-bis(1,1-dimethylpropyl)phenoxy)-benzanilide, 5-amino-2-(2-(1,1-dimethyl-ethyl)-4-methoxyphenoxy)-benzanilide, 4'-(1,1-dimethylethyl)-5-amino-2-(2,4-bis(1,1-dimethylpropyl)phenoxy)-benzanilide and 4'-amino-5-amino-2-(2,4-bis(1,1-dimethylpropyl)phenoxy)-benzanilide.

* * * * *